United States Patent [19]
Bombardelli

[11] Patent Number: 5,777,136
[45] Date of Patent: Jul. 7, 1998

[54] PROCESS FOR THE GLYCOSIDATION OF COLCHICINE DERIVATIVES AND THE PRODUCTS OBTAINED THEREBY

[75] Inventor: Ezio Bombardelli, Milan, Italy

[73] Assignee: Indena S.p.A., Milan, Italy

[21] Appl. No.: 796,317

[22] Filed: Feb. 7, 1997

[30]    Foreign Application Priority Data

Feb. 8, 1996 [IT] Italy ................. MI96A0236

[51] Int. Cl.$^6$ ................................. C07D 309/02
[52] U.S. Cl. ................................. 549/417; 549/418
[58] Field of Search ................................. 549/417, 418

[56]          References Cited

U.S. PATENT DOCUMENTS

| | | | |
|---|---|---|---|
| 3,816,396 | 6/1974 | Bardoneschi | 564/222 |
| 4,692,463 | 9/1987 | Brossi | 514/463 |
| 5,175,342 | 12/1992 | Brossi | 560/139 |

OTHER PUBLICATIONS

European Search Report, 1997.

Primary Examiner—Zinna Northington Davis
Attorney, Agent, or Firm—Pennie & Edmonds LLP

[57]          ABSTRACT

A process for the preparation of compounds having the formula

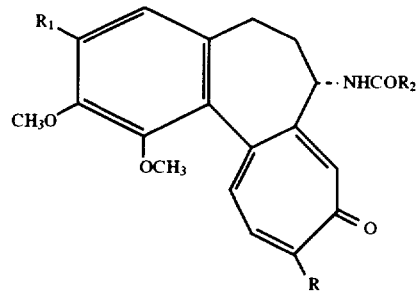

wherein:

R is a methoxy or thiomethyl group;
$R_1$ is a β-D-glycopyranosyloxy or 6-deoxygalactopyranosyloxy residue; and
$R_2$ is a $C_1$–$C_7$ alkyl group which process comprises reacting a protected material selected from the group consisting of derivatives of 1-fluoroglucose and 1-fluorofucose with a compound having the formula

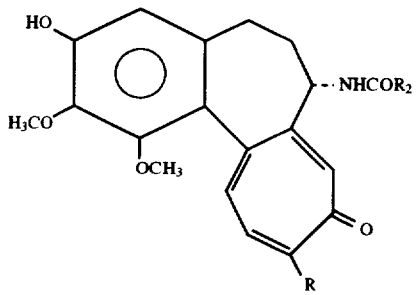

wherein R and $R_2$ are as defined above to form a crude reaction product containing at least one compound of formula (I).

20 Claims, No Drawings

PROCESS FOR THE GLYCOSIDATION OF COLCHICINE DERIVATIVES AND THE PRODUCTS OBTAINED THEREBY

TECHNICAL FIELD

The present invention relates to a process for the preparation of colchicine and thiocolchicine glycosides and derivatives thereof.

The invention further relates to novel colchicine and thiocolchicine derivatives obtainable by the process herein described.

BACKGROUND OF THE INVENTION

Colchicine is a pseudo alkaloid which has been widely used for a long time in therapy for the treatment of gout. Equally well known is the therapeutic use of 3-demethyl-thiocolchicine glucoside, i.e., thiocolchicoside, as a muscle relaxing agent and in treating inflammation of skeletal muscles. 3-Demethylcolchicine glycoside, or colchicoside, is known and studied for pharmacological purposes as well.

Therefore, an efficient method for the glycosidation of colchicine-skeleton molecules, to facilitate the preparation of both known compounds and novel derivatives for use in pharmacological research, would be very beneficial.

The presently known methods for carrying out this process have proved to be unsatisfactory. For example, FR 2112131 discloses a process for the glycosidation of thiocolchicine which comprises reacting acetobromoglucose (or 2,3,4,6-tetra-o-acetyl)-α,D-glycopyranosyl bromide) with 2-demethyl-colchicine or 3-demethyl-thiocolchicine.

This method is industrially unsatisfactory due to the low yield of product produced, the requirement for an excessive amount of the acetobromoglucose starting material and the length of time required for the reaction, i.e., at last 20 hours.

SUMMARY OF THE INVENTION

It has now been discovered that the use of fluoride compounds having a glycide moiety, wherein the hydroxy groups are suitably protected, as a starting component overcomes the drawbacks of prior art glycosidation methods described above.

The invention therefore relates, in a first embodiment, to a process for preparing compounds having the general formula:

wherein:
R is a methoxy or thiomethyl group;
$R_1$ is an optionally protected β-D-glycopyranosyloxy or 6-deoxygalactopyranosyloxy residue; and
$R_2$ is a $C_1$–$C_7$ alkyl group, preferably a methyl group.

The process of the invention comprises forming the compounds of Formula (I) above by reacting a suitably protected 1-fluoroglucose or 1-fluorofucose with a compound having the general formula:

wherein R and $R_2$ are as defined above, optionally followed by the cleavage of any protecting groups present on the glycide residue. 1-fluoroglucose and fucose derivatives are typically protected by acetyl groups, i.e., forming respectively, fluoroacetoglucose (2,3,4,6-tetra-O-acetyl-α, D-glycopyranosyl fluoride) and fluoroacetofucose (1,2,3,4-tetra-O-acetyl-α, L-fucopyranosyl fluoride). Thus, the final step of the method of the invention is the (optional) removal of the protective acetyl groups.

The invention is further directed, in a second embodiment, to novel colchicine and thiocolchicine derivatives produced by the method described above.

DETAILED DESCRIPTION OF THE INVENTION

The first embodiment of the invention involves reacting a suitably protected (e.g., by acetyl groups) 1-fluoroglucose or 1-fluorofucose with a compound having the formula followed by optionally cleaving any protective groups present on the glycide residue, to form a colchicine or thiocolchicine glycoside (or a derivative thereof) having the formula wherein:
R is a methoxy or thiomethyl group;
$R_1$ is an optionally protected β-D-glycopyranosyloxy or 6-deoxygalactopyranosyloxy residue; and $R_2$ is a $C_1$–$C_7$ alkyl group, preferably a methyl group.

The reaction is preferably carried out in a solvent selected from acetonitrile, nitromethane, halogenated hydrocarbons and mixtures thereof. The use of acetonitrile is particularly preferred. The reaction is carried out for a time ranging from 10 minutes to one hour, preferably between about 15 and 40 minutes, at temperatures from 0° C. to the solvent's reflux temperature, preferably at room temperature, under inert atmosphere and in the presence of a base. If desired, the step of recovering the protected glycoside product, for example, glycoside tetraacetate, can be bypassed by hydrolyzing the protecting groups directly on the crude product, to yield the pure product in high yields by direct crystallization. This was not possible with the methods of the prior art, due to the excessive quantity of acetobromoglucose required for carrying out the reaction.

3-(2'-3,4'-Tri-O-acetyl-L-fucopyranosyl)3-dimethylthiocolchicine is a product having useful pharmacological properties and it is a specific object of the invention.

Of course, it would be well recognized by those of ordinary skill in this art, that the presently described method is clearly capable of forming a variety of such novel derivatives and thus the invention is not limited to the specific example recited herein.

The process of the invention provides a variety of advantages over prior art methods of forming colchicine and thiocolchicine glycosides and derivatives thereof. These advantages include:

- comparatively short reaction times (generally 20–30 minutes);
- high yields, of about 90% or higher, without the need to use a great excess of the glycosylation agent;
- the stability of fluoroacetoglucose and fluoroacetofucose derivatives; and
- the relatively mild reaction conditions and the possibility of crystallizing the final product directly from the crude reaction product.

EXAMPLES

The following examples illustrate the invention in further detail. The invention is not limited, however, to the specific embodiments disclosed in the following examples.

Example 1 a) Synthesis of 2,3,4,6-tetra-O-acetyl-α, D-glycopyranosyl fluoride

In a 250 ml polyethylene flask, 1,2,3,4,6-penta-O-acetyl-β, D-glycopyranose (5 g) is dissolved in anhydrous toluene (30 ml). The mixture is cooled at −20° C. and 70% Py(HF)$_n$, in pyridine (10 mls.) is added. The material is mixed with a magnetic stirrer for about 12 hours, whereupon the temperature reaches 20° C. The progress of the reaction is checked by thin layer chromatography ("TLC") using an ethyl ether/methanol (3:1) system.

A saturated solution of NaF is added and the phases are partitioned; the aqueous phase is extracted twice with a saturated solution of KHCO$_3$ and with a saturated solution of NaCl. 2,3,4,6-Tetra-O-acetyl-αa,D- saturated solution. 2,3,4,6-Tetra-O-acetyl-αa,D-glycopyranosyl fluoride is crystallized from ethyl ether (60% yield), and shows physical and spectroscopical characteristics similar to those reported in literature.

b) Synthesis of thiocolchicoside

In a flask at room temperature under inert atmosphere, 3-demethylthiocolchicine (201 mg, 0.5 mmol) and 2,3,4,6-tetra-O-acetyl-α, D-glycopyranosyl fluoride (263 mg, 0.75 mmol) are suspended in anhydrous CH$_3$CN (10 ml).

The reaction mixture is added with 1,1,3,3-tetramethylguanidine (188 µl, 1.5 mmol). Following the addition of the base, the reagents are dissolved and the solution is colored in red.

Ether BF3 (502 pl, 8 mmol) is added and the mixture becomes lighter in color.

The reaction is continued with magnetic stirring and checked by TLC using a MeOH—CH$_2$Cl$_2$ 1:9 system. After 20 minutes the starting product is completely transformed. A KHCO$_3$ saturated solution is added and the phases are partitioned; the aqueous phase is extracted with AcOEt (3×10 ml). The combined organic phases are washed with a KHSO$_4$ saturated solution and a NaCl saturated solution. The mixture is dried over MgSO$_4$, filtered and the solvent is evaporated off, to obtain a solid crude product (562 mg) which is dissolved in ethanol (4 ml). 1N NAOH (2 ml) is added, with magnetic stirring. The progress of the reaction is checked by TLC: (MeOH—CH$_2$Cl$_2$/1:9). The reaction is complete within 3 hours. Thiocolchicoside (272 mg, 0.48 mmol) crystallizes directly from the reaction medium (97% yield).

Example 2 a) Synthesis of 2,3,4-tri-O-acetyl-α-L-fueopyranose (Ref.: G. A. Levvy, A. NcAllan, Biochem. J., 80 (1961) 35 433–439).

L-fucose (5 g) is added in about 20 minutes to a mixture of acetic anhydride (9.2 ml) and pyridine (11 ml), cooling at −5° C. The mixture is magnetically stirred, with the temperature maintained substantially constant for 4 hours and subsequently at 0° C. for 2 days, after that it is poured into ice and stirred for 4 hours, keeping the temperature at 0° C.

The mixture is extracted with CHCl$_3$ (3×25 ml). The combined organic phases are washed with 10% HCl, (6×100 ml), dried over MgSO$_4$, filtered and the solvent is evaporated off, to obtain a solid crude product (2.05 g) which is crystallized from Et$_2$O-iPr$_2$O (1–9 g. 93%). TLC: (AcOEt-Cyclohexane/3:2); the assignment of the absolute configuration of the anomeric carbon is performed by IH NMR: in fact, a $^3J_{1,2}$=3.4 Hz is observed, corresponding to an axial-equatorial cis coupling. M.p.=75–76° C.

The resulting fucose tetraacetate is transformed into the corresponding 1-fluoro derivative by treatment with pyridinium polyhydrogen fluoride (2 ml for 1 g of sugar) in anhydrous toluene, in a manner analogous to that described above for glucose (R. Noyori et al., Chem. Lett., (1984) 1747–1750), maintaining the temperature at 5° C. for 7 hours.

b) Synthesis of 3-(2',3',4'-tri-O-acetyl-L-fucopyranosyl)3-demethylthiocolchicine Operating at room temperature under inert atmosphere, 3-demethylthiocolchicine (88 mg, 0. 22 mmol) and 1-fluoroacetofucose (100 mg, 0.33 mmol) are suspended in anhydrous CH 3CN (10 ml). The reaction mixture is combined with 1,1,3,3-tetramethylguanidine (83 µl, 0.66 mmol). Following the addition of the base, the reagents are dissolved and the solution is colored in red. Ether BF3 (221 µl, 1.76 mmol) is added and the mixture becomes lighter in color. The reaction mixture is magnetically stirred, and checked by TLC: (MeOH—CH$_2$Cl$_2$/0.5:10). The reaction is complete within 30 minutes. A KHCO$_3$ saturated solution is added and the phases are partitioned; the aqueous phase is extracted with AcOEt. The combined organic phases are washed with a solution of saturated KHSO$_4$ and a solution of saturated NaCl, dried over MgSO$_4$, filtered and the solvent is evaporated off, to obtain a solid crude product (202 mg) which is purified by gravimetric chromatography (MeOH—CH$_2$Cl$_2$/0.5:10). The resulting product (135 mg 0.20 mmol, 90%) is identified by $^1$H NMR. Fucoside triacetate is then dissolved in ethanol (2 ml), 1.5 ml of 1N NaOH is added and magnetically stirred. The progress of the reaction is checked by TLC: (MeOH—$CH_2Cl_2$/1:9). The reaction is completed within 1 hour. Fucoside (272 mg, 0.48 mmol, 90%) crystallizes directly from the reaction medium (m.p. 202° C.; $[a]^{22}D=-188$ (cl, MeOH).

What is claimed is:

1. A process for the preparation of compounds having the formula

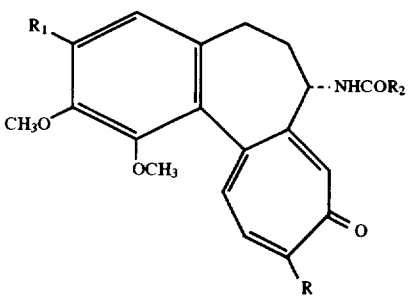

(I)

wherein:

R is a methoxy or methylthio group;

$R_1$, is a β-D-glycopyranosyloxy or 6-deoxygalactopyranosyloxy residue; and $R_2$ is a $C_1$–$C_7$ alkyl group which process comprises reacting a protected material selected from the group consisting of derivatives of 1-fluoroglucose and 1-fluorofucose with a compound having the formula

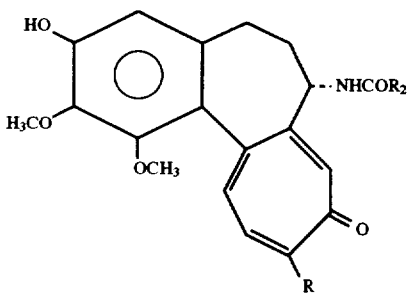

(II)

wherein R and $R_2$ are as defined above to form a crude reaction product containing at least one compound of formula (I).

2. The process of claim 1 which further comprises separating from said crude reaction product a relatively purified protected glycoside product.

3. The process of claim 2 wherein said purification step is accomplished by a direct crystallization process.

4. The process of claim 1 which further comprises cleaving substantially any protective groups present in said crude reaction product.

5. The process of claim 4 wherein said protective groups are cleaved by hydrolyzing said crude product.

6. The process of claim 2 which further comprises cleaving substantially any protective groups present on said relatively purified protected glycoside product.

7. The process of claim 6 wherein said protective groups are cleaved by hydrolyzing said relatively purified product.

8. The method of claim 1 wherein R is $SCH_3$.

9. The method of claim 1 wherein $R_2$ is a methyl group.

10. The method of claim 1 which further comprises choosing 2,3,4,6-tetra-O-acetyl-α-D-glycopyranosyl fluoride as the derivative of said 1-fluoroglucose.

11. The method of claim 1 which further comprises choosing 2,3,4-tri-O-acetyl-α-L-fucopyranosyl fluoride as the derivative of said 1-fluorofucose.

12. The method of claim 1 in which the reaction is carried out in a solvent selected from the group consisting of acetonitrile, nitromethane, halogenated hydrocarbons and mixtures thereof.

13. The method of claim 12 wherein the reaction is carried out in a solvent comprising acetonitrile.

14. The method of claim 12 which further comprises carrying out said reaction at a temperature of between about 0° C. and a reflux temperature of said solvent.

15. The method of claim 1 wherein the reaction is permitted to continue for a time of between about 10–60 minutes.

16. The method of claim 15 wherein the reaction is permitted to continue for a time of between about 15 and 40 minutes.

17. The method of claim 1 which further comprises carrying out said reaction in an inert atmosphere.

18. The method of claim 1 which further comprises adding a sufficient amount of a basic material to the reaction mixture to adjust the pH thereof to a value of >7.

19. 3-(2'-3',4'-Tri-O-acetyl-L-fucopyranosyl)-3-demethylthiocolchicine.

20. 3-L-fucopyranosyl-3-demethylthio-colchicine.

* * * * *